(12) United States Patent
Baert et al.

(10) Patent No.: US 8,916,558 B2
(45) Date of Patent: Dec. 23, 2014

(54) POWDERS FOR RECONSTITUTION

(75) Inventors: Lieven Elvire Colette Baert, Brugge (BE); Elke Van Gyseghem, Vilvoorde (BE); Guy René Jaak Van Den Mooter, Pellenberg (BE); Peter Jozef Maria Van Remoortere, Kapellen (BE)

(73) Assignee: Tibotec Pharmaceuticals Ltd., Eastgate Village, Eastgate Little Island, Co Cork (IE)

( * ) Notice: Subject to any disclaimer, the term of this patent is extended or adjusted under 35 U.S.C. 154(b) by 485 days.

(21) Appl. No.: 12/530,665

(22) PCT Filed: Mar. 14, 2008

(86) PCT No.: PCT/EP2008/053056
§ 371 (c)(1),
(2), (4) Date: Sep. 10, 2009

(87) PCT Pub. No.: WO2008/110619
PCT Pub. Date: Sep. 18, 2008

(65) Prior Publication Data
US 2010/0120795 A1  May 13, 2010

(30) Foreign Application Priority Data

Mar. 14, 2007 (EP) .................................... 07104082

(51) Int. Cl.
| | | |
|---|---|---|
| *A61K 31/50* | (2006.01) | |
| *A61K 9/00* | (2006.01) | |
| *A61K 9/16* | (2006.01) | |
| *A61K 9/08* | (2006.01) | |

(52) U.S. Cl.
CPC ............. *A61K 9/0095* (2013.01); *A61K 9/1635* (2013.01); *A61K 9/08* (2013.01); *Y10S 514/934* (2013.01)
USPC ............ 514/247; 514/516; 514/579; 514/934

(58) Field of Classification Search
USPC .................................. 514/247, 516, 579, 934
See application file for complete search history.

(56) References Cited

U.S. PATENT DOCUMENTS

| | | | |
|---|---|---|---|
| 5,182,111 | A | 1/1993 | Aebischer et al. |
| 5,368,864 | A | 11/1994 | Lahr et al. |
| 5,705,270 | A | 1/1998 | Soon-Shiong et al. |
| 6,045,829 | A | 4/2000 | Liversidge et al. |
| 6,221,400 | B1 | 4/2001 | Liversidge et al. |
| 7,887,845 | B2 | 2/2011 | Verreck et al. |
| 2001/0026804 | A1 | 10/2001 | Boutignon |
| 2002/0009493 | A1 | 1/2002 | Schwendeman et al. |
| 2004/0082937 | A1 | 4/2004 | Ausiello et al. |
| 2004/0115268 | A1 | 6/2004 | Ashton et al. |
| 2004/0198739 | A1 * | 10/2004 | Guillemont et al. ..... 514/252.02 |
| 2005/0163855 | A1 | 7/2005 | Cho et al. |
| 2006/0269475 | A1 | 11/2006 | Ryu et al. |
| 2008/0081064 | A1 | 4/2008 | Jelle et al. |
| 2011/0257111 | A1 | 10/2011 | Harbeson et al. |

FOREIGN PATENT DOCUMENTS

| | | |
|---|---|---|
| EP | 0489181 B1 | 7/1991 |
| EP | 0 489 181 A1 | 10/1996 |
| EP | 0 499 299 B1 | 8/2000 |
| EP | 1 350 792 A1 | 10/2003 |
| EP | 1350792 | 10/2003 |
| EP | 1 214 059 B1 | 5/2005 |
| EP | 1 632 232 A1 | 3/2006 |
| JP | 06-316524 | 11/1994 |
| WO | WO 93/23021 A2 | 11/1993 |
| WO | WO 96/01110 A2 | 1/1996 |
| WO | WO 01/74329 A2 | 10/2001 |
| WO | WO 02/30482 A1 | 4/2002 |
| WO | WO 03/00235 A1 | 1/2003 |
| WO | WO 03/016306 A1 | 2/2003 |
| WO | WO 03/43586 A2 | 5/2003 |
| WO | WO 2004/016581 A1 | 2/2004 |
| WO | WO 2004/043433 A2 | 5/2004 |
| WO | WO 2004/046143 A1 | 6/2004 |
| WO | WO 2004/050058 A2 | 6/2004 |
| WO | WO 2004/069812 A1 | 8/2004 |
| WO | WO 2005/021001 A1 | 3/2005 |
| WO | WO 2005/123076 A2 | 12/2005 |
| WO | WO 2006/024668 A1 | 3/2006 |
| WO | WO 2006/026500 A1 | 3/2006 |
| WO | WO 2006/055603 A2 | 5/2006 |
| WO | WO 2006/106103 A2 | 10/2006 |
| WO | WO 2006/108828 A1 | 10/2006 |
| WO | WO 2006/131806 A2 | 12/2006 |
| WO | 2007/014393 | 2/2007 |
| WO | WO 2007/014393 A2 | 2/2007 |
| WO | WO 2007/082922 A2 | 7/2007 |
| WO | WO2007/141308 A1 | 12/2007 |
| WO | WO 2007/147882 A3 | 12/2007 |

(Continued)

OTHER PUBLICATIONS

International Search Report for related application No. PCT/EP2008/053056 mailed Sep. 1, 2008.
Farquhar, et al., "Salivary Secretory Leukocyte Protease Inhibitor Is Associated with Reduced Transmission of Human Immunodeficiency Virus Type 1 Through Breast Milk," The Journal of Infectious Diseases, 186: 1173-1176 (2002).
Janssen, et al., "In Search of a Novel Anti-HIV Drug: Multidisciplinary Coordination in the Discovery of 4-[[4-[[4-(1E)-2-Cyanoethenyl]-2,6-dimethylphenyl]amino]2-pyrimidinyl]amino]benzonitrile (R278474, Rilpivirine)," Journal of Molecular Chemistry, 48: 1901-1909 (2005).

(Continued)

*Primary Examiner* — Renee Claytor
*Assistant Examiner* — Shobha Kantamneni
(74) *Attorney, Agent, or Firm* — Kirk Baumeister; Rajiv S. Shah (57) ABSTRACT

This invention relates to powders for reconstitution comprising the NNRTI TMC278 dispersed in certain water-soluble polymers, which can be used in the treatment of HIV infection.

2 Claims, 1 Drawing Sheet

(56) References Cited

FOREIGN PATENT DOCUMENTS

| WO | WO 2008/110619 A1 | 6/2008 |
|---|---|---|
| WO | WO 2009/007441 A3 | 1/2009 |
| WO | WO 2009/046299 A3 | 4/2009 |

OTHER PUBLICATIONS

Merisko-Liversridge, et al., "Nanosizing: a formulation approach for poorly-water-soluble compounds," European Journal of Pharmaceutical Science, 18: 113-120 (2003).

McNeely, et al., "Secretory Leukocyte Protease Inhibitor: A Human Saliva Protein Exhibiting Anti-Human Immunodeficiency Virus 1 Activity In Vitro," The Journal of Clinical Investigation, 96: 456-464 (1995).

Muller, et al., "Nanosuspensions as particulate drug formulations in therapy Rationale for development and what we can expect for the future," Advanced Drug Delivery Reviews, 47: 3-19 (2001).

Okwundu, et al., "Antiretroviral pre-exposure prophylaxis (PrEP) for preventing HIV in high-risk individuals," The Cochran Library, 4: 1-23 (2009).

Patel, et al., "Poloxamers: A pharmaceutical excipients with therapeutic behaviors," International Journal of PharmTech Research, 1(2): 299-303 (2009).

Rabin, et al., "In vitro and in vivo demonstration of risperidone implants in mice," Schizophrenia Research, 98: 66-78 (2008).

Smith, et al., "An assessment of the use of Implanon® in three community services," The Journal of Family Planning and Reproductive Health Care, 28(4): 193-196 (2002).

Susman, et al., Retroviruses and Opportunistic Infections—12$^{th}$ Conference, IDrugs, 8(4): 299-302 (2005).

Wahl, et al., American Journal of Pathology, 150(4): 1275-1284 (1997).

PCT International Search Report in WO 2005/021005 dated Feb. 7, 2005.

PCT International Search Report in WO 2011/080141 dated Dec. 19, 2011.

PCT International Search Report in PCT/EP2008/059054 dated Feb. 24, 2009.

PCT International Search Report in WO 2005/021001 dated Jul. 2, 2005.

Harry G. Brittain, "Polymorphism in Pharmaceutical Solids," Chapter 1, pp. 1-10.

Harry G. Brittain, "Polymorphism in Pharmaceutical Solids," Chapter 5, pp. 183-226.

Bryn, et al., "Solid-State Pharmaceutical Chemistry," Chem. Mater., 6: 1148-1158 (1994).

Gregoriadis, et al., "Targeting of Drug 6 Strategies for Stealth Therapeutic Systems," vol. 300, pp. 4-5 (1998).

Guillemont, et al., "Synthesis of Novel Diarylpyrimidine Analogues and their Antiviral Activity against Human Imunodeficiency Virus Type 1," Journal of Medicinal Chemistry, 48: 2072-2079 (2005).

Marcus, et al., "HIV: epidemiology and strategies for therapy and vaccination," Intervirology, 45(4-6): 260-266 (2002). Abstract Only.

Silvestri, et al., "Current state-of-the-art in preclinical and clinical development of novel non-nucleotide HIV-1 reverse transcriptase inhibitors," Expert Opinion on Therapeutic Patents, 16(7): 939-962 (2006) Abstract Only.

Van Heeswijk, et al., "Combination of protease inhibitors for the treatment of HIV-1-infected patients: a review of pharmacokinetics and clinical experience," Antiviral therapies, 6(4): 201-229 (2001).

* cited by examiner

Mean plasma concentration (ng/ml) *versus* time profiles of TMC278 in fasted male beagle dog after single oral administration of 3 different formulations.

POWDERS FOR RECONSTITUTION

CROSS REFERENCE TO RELATED APPLICATIONS

This application is a national stage application of Patent Application No. PCT/EP2008/053056, filed Mar. 14, 2008, which application claims priority from EPO Patent Application No. 07104082.8, filed Mar. 14, 2007.

FIELD OF THE INVENTION

This invention relates to powders for reconstitution comprising the NNRTI TMC278 dispersed in certain water-soluble polymers, useful in the treatment of HIV infection.

BACKGROUND OF THE INVENTION

The treatment of Human Immunodeficiency Virus (HIV) infection, known as cause of the acquired immunodeficiency syndrome (AIDS), remains a major medical challenge. HIV is able to evade immunological pressure, to adapt to a variety of cell types and growth conditions, and to develop resistance against currently available drug therapies. The latter include nucleoside reverse transcriptase inhibitors (NRTIs), non-nucleoside reverse transcriptase inhibitors (NNRTIs), nucleotide reverse transcriptase inhibitors (NtRTIs), HIV-protease inhibitors (PIs), and the more recent fusion inhibitors.

Although effective in suppressing HIV, each of these drugs, when used alone, is confronted with the emergence of resistant mutants. This led to the introduction of combination therapy of several anti-HIV agents usually having a different activity profile. In particular the introduction of "HAART" (Highly Active Anti-Retroviral Therapy) resulted in a remarkable improvement in anti-HIV therapy, leading to a large reduction in HIV-associated morbity and mortality. Current guidelines for antiretroviral therapy recommend such triple combination therapy regimen even for initial treatment. However, none of the currently available drug therapies is capable of completely eradicating HIV. Even HAART can face the emergence of resistance, often due to non-adherence to and non-persistence with antiretroviral therapy. In these cases HAART can be made effective again by replacing one of its components by one of another class. If applied correctly, treatment with HAART combinations can suppress the virus for many years, up to decades, to a level where the outbreak or progress of AIDS is stopped.

One class of HIV drugs often used in HAART is that of the NNRTIs, a number of which are currently on the market and several others are in various stages of development. An NNRTI currently in development is the compound 4-[[4-[[4-(2-cyano-ethenyl)-2,6-dimethylphenyl]-amino]-2-pyrimidinyl]-amino]-benzonitrile, also referred to as TMC278. This compound not only shows pronounced activity against wild type HIV, but also against many of its mutated variants. The compound TMC278, its pharmacological activity as well as a number of procedures for its preparation have been described in WO 03/16306. Various conventional pharmaceutical dosage forms, including tablets, capsules, drops, suppositories, oral solutions and injectable solutions are exemplified therein.

Infants and children constitute a growing group of HIV infected patients. Paediatric anti-HIV medication poses particular challenges in that the dose regimens vary to a large extent due to variations in age and body weight (babies—children). Especially in the first year after birth, an infant undergoes rapid changes and body weight increases spectacularly. Because of these rapid changes at young age, dosing of a drug needs to be adjusted frequently and dosage forms need to offer flexibility in dosing. Traditional dosage forms such as pills and capsules lack the dosing flexibility required in paediatric applications. Moreover, these dosage forms are not fit for administration to young children and especially to infants in which case drinkable formulations are the preferred route of administration. These comprise liquid formulations such as syrups as well as dry formulations such as powders for reconstitution in which the drug is distributed in dry form and is converted in liquid form by adding water.

Powders for reconstitution are attractive over liquid oral dosage forms because of their compactness making them more convenient to store and transport. Incorporating TMC278 in a powder for reconstitution poses particular challenges in that it is poorly soluble in water. Upon addition of water, only a limited amount is dissolved not resulting in effective uptake of the active ingredient. Converting the free base form into an acid-addition salt can increase the solubility of this active agent, but only the salt forms with strong acids such as hydrochloric acid, show workable solubility profiles. For paediatric applications these salts are unattractive because of their low pH. Hence the challenge is to provide a powder of reconstitution using the base form of TMC278 that upon addition of water results in a dosage form that has effective therapeutic concentrations of the active.

It now has been found that the NNRTI TMC278 can be converted into a powder for reconstitution that allows a flexible application of the active ingredient and moreover is fit for paediatric applications. The powders for reconstitution of this invention may also be applied in adult patient groups that have difficulty or find inconvenience in swallowing, for example the elderly. The powders for reconstitution of this invention may contain several active ingredients thereby allowing the administration of drug cocktails in one administration. This results in a reduced number of administrations thereby being beneficial in terms of pill burden and drug compliance of the patient.

DESCRIPTION OF THE INVENTION

In one aspect the present invention relates to the use of a powder comprising TMC278, dispersed in a water-soluble polymer selected from polyvinylpyrrolidone, a copolymer of vinylpyrrolidone and vinyl acetate, a hydroxyalkyl alkylcellulose, and a poloxamer, to be mixed with water, for the manufacture of a medicament for the treatment of a subject infected with HIV. In one embodiment said powder is obtained by spray-drying.

In a further aspect there is provided a method of treating a patient infected with HIV, said method comprising the administration to said patient of a powder comprising TMC278, dispersed in a water-soluble polymer selected from polyvinylpyrrolidone, a copolymer of vinylpyrrolidone and vinyl acetate, a hydroxyalkyl alkylcellulose, and a poloxamer, wherein prior to administration the powder is mixed with water. The amount of TMC278 in said powder is preferably an anti-virally effective amount.

In a further aspect there is provided a supersaturated solution of TMC278 and a water-soluble polymer selected from polyvinylpyrrolidone, a copolymer of vinylpyrrolidone and vinyl acetate, a hydroxyalkyl alkylcellulose, and a poloxamer, in an aqueous medium. Said supersaturated solution can be obtained by adding water to a powder comprising an anti-virally effective amount of TMC278 dispersed in a water-soluble polymer selected from polyvinylpyrrolidone, a copolymer of vinylpyrrolidone and vinyl acetate, a hydroxyalkyl alkylcellulose, and a poloxamer. In an alternative aspect there is provided a supersaturated solution of TMC278 and a water-soluble polymer selected from polyvinylpyrrolidone, a copolymer of vinylpyrrolidone and vinyl acetate, a hydroxyalkyl alkylcellulose, and a poloxamer, obtainable or obtained by adding water to a powder comprising an anti-virally effective amount of TMC278 dispersed in a water-soluble polymer selected from polyvinylpyrrolidone, a copolymer of vinylpyrrolidone and vinyl acetate, a hydroxyalkyl alkylcellulose, and a poloxamer.

In another aspect, there is provided a method for the treatment of a subject infected with HIV, said method comprising the administration of a supersaturated solution of TMC278 and a water-soluble polymer selected from polyvinylpyrrolidone, a copolymer of vinyl-pyrrolidone and vinyl acetate, a hydroxyalkyl alkylcellulose, and a poloxamer, in an aqueous medium.

The invention furthermore provides a method of, or alternatively, a process for preparing a supersaturated solution of TMC278 and a water-soluble polymer selected from polyvinylpyrrolidone, a copolymer of vinylpyrrolidone and vinyl acetate, a hydroxyalkyl alkylcellulose, and a poloxamer, in an aqueous medium, said method or process comprising adding water to TMC278, dispersed in a water-soluble polymer selected from polyvinylpyrrolidone, a copolymer of vinylpyrrolidone and vinyl acetate, a hydroxyalkyl alkylcellulose and a poloxamer. In one embodiment the supersaturated solution is prepared by adding water to a powder of TMC278, dispersed in a water-soluble polymer selected from polyvinylpyrrolidone, a copolymer of vinylpyrrolidone and vinyl acetate, a hydroxyalkyl alkylcellulose, and a poloxamer.

The compound used in the invention is 4-[[4-[[4-(2-eyano-ethenyl)-2,6-dimethyl-phenyl]amino]-2-pyrimidinyl]amino] benzonitrile, having the generic name rilpivirine, also known as TMC278 (or previously referred to as R278474), TMC278 is in clinical development as an HIV inhibitor of the NNRTI class.

TMC278 occurs in stereoisomeric forms, more in particular as E- and Z-isomeric forms. Both isomers may be used in the present invention. Whenever reference is made herein to TMC278, the E- or the Z-form as well as any mixture of both forms are meant to be included. A preferred form of TMC278 for use in the invention is the E-isomer, i.e. (E)-4-[[4-[[4-(2-cyanoethenyl)-2,6-dimethylphenyl]-amino]-2-pyrimidinyl]-amino]-benzonitrile, which may be referred to as E-TMC278. The Z-isomer of TMC278, i.e. (Z)-4-[[4-[[4-(2-cyanoethenyl)-2,6-dimethylphenyl]-amino]-2-pyrimidinyl]amino]-benzonitrile, which may be referred to as Z-TMC278), can also be used.

Whenever reference is made herein to the E-form of TMC278 (i.e. E-TMC278), the pure E-isomer or any isomeric mixture of the E- and the Z-forms wherein the E-form is predominantly present is meant to be comprised, i.e. an isomeric mixture containing more than 50% or in particular more than 80% of the E-form, or even more than 90% of the E-form. Of particular interest is the E-form substantially free of the Z-form. Substantially free in this context refers to E-Z-mixtures with no or almost no Z-form, e.g. isomeric mixtures containing as much as 90%, in particular 95% or even 98% or 99% of the E-form. Equally, whenever reference is made herein to the Z-form of TMC278 (i.e. Z-TMC278), the pure Z-isomer or any isomeric mixture of the Z- and the E-forms wherein the Z-form is predominantly present is meant to be comprised, i.e. an isomeric mixture containing more than 50% or in particular more than 80% of the Z-form, or even more than 90% of the Z-form. Of particular interest is the Z-form substantially free of the E-form. Substantially free in this context refers to E-Z-mixtures with no or almost no E-form, e.g. isomeric mixtures containing as much as 90%, in particular 95% or even 98% or 99% of the Z-form.

Whenever used herein, the term "TMC278" refers to as well stereoisomeric forms of TMC278 as well as any mixtures of said stereoisomeric forms. In particular, the term "TMC278" refers to the E-isomer of TMC278.

The powders for reconstitution for use in the present invention comprise the active ingredient TMC278 dispersed in particular water-soluble polymers, which may be referred to as a solid dispersion of the active ingredient TMC278 in the particular water-soluble polymers. The latter include polyvinylpyrrolidone (PVP) and copolymers of vinylpyrrolidone and vinyl acetate (PVPCoVA, sometimes also refereed to as PVP-VA); hydroxyalkyl alkylcelluloses, in particular hydroxy$C_{1-4}$alkyl $C_{1-4}$alkyl-celluloses such as hydroxypropylmethylcellulose (HPMC), and poloxamers, in particular poloxamer P407.

The amount of water-soluble polymer in the solid dispersion of TMC278 in the particular water-soluble polymers may be in the range from about 50% to about 99%, in particular about 70% to about 98%, or about 80% to about 95% or about 85% to about 95%, e.g. about 90%, by weight relative to the total weight of the solid dispersion. The weight: weight ratio of water-soluble polymer to TMC278 in the solid dispersion of TMC278 in the particular water-soluble polymers may be in the range of about 50:1 to about 1:1, or about 20:1 to about 1:1, or about 10:1 to about 1:1, or about 10:1 to about 5:1, for example said weight:weight ratio is about 9:1. The amount of TMC278 in the solid dispersion of TMC278 in the particular water-soluble polymers may be in the range from about 1% to about 40%, in particular about 1% to about 30%, or about 1% to about 20% or about 5% to about 15%, e.g. about 10%, by weight relative to the total weight of the solid dispersion.

The powders for reconstitution for use in the present invention may comprise the solid dispersion of the active ingredient TMC278 in the particular water-soluble polymers in amount that may be in the range from about 60% to about 100%, in particular about 70% to about 100%, or about 80% to about 100% or about 90% to about 100%, by weight relative to the total weight of the powder for reconstitution. Other ingredients may be present, such as the ingredients mentioned hereinafter, in an amount that makes up the remainder of the powder for reconstitution, in particular in an amount that may be in the range from about 0% to about 40%, in particular about 0% to about 30%, or about 0% to about 20% or about 0% to about 10%, by weight relative to the total weight of the powder for reconstitution.

As used herein the term $C_{1-4}$alkyl defines saturated hydrocarbon radicals having from 1 to 4 carbon atoms, such as methyl, ethyl, 1-propyl 2-propyl, 1-butyl, 2-butyl, 2-methyl-2-propyl, 2-methyl-1-propyl.

In one embodiment, the water-soluble polymer has a molecular weight in the range 500 D to 2 MD. The water-soluble polymer may have an apparent viscosity of 1 to 15,000 mPa.s, or of I to 5000 mPa.s, or of 1 to 700 mPa.s, or of 1 to 100 mPa.s when in a 2% (w/v) aqueous solution at 20° C.

Particular hydroxyalkyl alkylcelluloses include hydroxyethyl methylcellulose and hydroxypropyl methylcellulose (or HPMC, e.g. HPMC 2910 15 mPa.s; HPMC 2910 5 mPa.s). Particular vinylpyrrolidones include PVP K29-32, PVP K90.

Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule. A preferred HPMC is hypromellose 2910 15 mPa.s or hypromellose 2910 5 mPa.s, especially hypromellose 2910 15 mPa.s. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxy groups and the third and fourth digits the approximate percentage composition of hydroxypropoxyl groups; 15 mPa.s or 5 mPa.s is a value indicative of the apparent viscosity of a 2% aqueous solution at 20° C.

Copolymers of vinylpyrrolidone and vinyl acetate that may be used include those copolymers wherein the molecular ratio of the monomers vinylpyrrolidone to vinyl acetate is about 1.2 or wherein the mass ratio of the monomers vinylpyrrolidone to vinyl acetate is about 3:2. Such copolymers are commercially available and are known as eopovidone or copolyvidone, sold under trademarks Kolima™ or Kollidon VA 64™. The molecular weight of these polymers may be in the range of about 45 to about 70 kD. The K-value, obtained from viscosity measurements may be in the range of about 25 to about 35, in particular the K value may be about 28.

Polyvinylpyrrolidine polymers that may be used are known as povidone (PVP) and are commercially available. They may have a molecular weight that is in the range of about 30 kD to about 360 kD. Examples are PVP K25 (BASF, MW=29.000), PVP K30 (BASF, MW=40.000), and PVP K90 (BASF, MW=360.000), available under the tradename Kolidon™.

Poloxamers are nonionic triblock copolymers composed of a central hydrophobic chain of polyoxypropylene (polypropylene oxide) flanked by two hydrophilic chains of polyoxyethylene (polyethylene oxide), with varying lengths of the polymer blocks. For the generic term "poloxamer", these copolymers are commonly named with the letter "P" (for poloxamer) followed by three digits, the first two digits× 100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). Poloxamers are commercially available under the tradename Pluronic™. For the Pluronic tradename, coding of these copolymers starts with a letter to define its physical form at room temperature (L=liquid, P=paste, F=flake (solid)) followed by two or three digits, the first digit(s) refer to the molecular mass of the polyoxypropylene core and the last digit×10 gives the percentage polyoxyethylene content (e.g., F127=Pluronic™ with a polyoxypropylene molecular mass of 4,000 g/mol and a 70% polyoxyethylene content). Pluronic™ F127 corresponds to poloxamer P407 (P407).

The active ingredient TMC278 may be dispersed more or less evenly throughout the water-soluble polymer or can be dispersed uniformly or homogenously throughout the polymer. In the former instance the active ingredient is dispersed less homogenous throughout the polymer. There may be domains or small regions wherein amorphous, microcrystalline or crystalline compound of formula (I), or amorphous, micro-crystalline or crystalline water-soluble polymer, or both, are dispersed more or less evenly in the water-soluble polymer.

Various techniques exist for preparing solid dispersions including melt-extrusion, spray-drying and solution-evaporation.

The solution-evaporation process comprises the following steps:
  a) dissolving TMC278 and the water-soluble polymer in an appropriate solvent, optionally at elevated temperature;
  b) allowing the solvent in the solution obtained in step a) to evaporate, optionally by heating, or optionally under vacuum, or both, until dry material is obtained.

The solution may also be poured onto a large surface so as to form a thin film, and the solvent evaporated therefrom.

The melt-extrusion process usually comprises the following steps:
  a) mixing TMC278 and the water-soluble polymer,
  b) optionally blending additives with the thus obtained mixture,
  c) heating and compounding the thus obtained blend until one obtains a homogeneous melt,
  d) forcing the thus obtained melt through one or more nozzles; and
  e) cooling the melt until it solidifies.

The terms "melt" and "melting" should be interpreted broadly. These terms not only mean the alteration from a solid state to a liquid state, but can also refer to a transition to a glassy state or a rubbery state, and in which it is possible for one component of the mixture to get embedded more or less homogeneously into the other. In particular cases, one component will melt and the other component(s) will dissolve in the melt thus forming a solution, which upon cooling may form a solid solution having advantageous dissolution properties.

After preparing the solid dispersions as described hereinabove, the obtained products are milled and optionally sieved. The solid dispersion product may be milled or ground to particles having a particle size of less than 600 µm, or less than 400 µm, or less than 125 µm, or to the particle sizes mentioned hereinafter.

A preferred process to prepare the powders for reconstitution for use in the present invention is by the spray-drying technique. In the spray-drying technique, TMC278 and the water-soluble polymer are dissolved in an appropriate solvent and the resulting solution is then sprayed through the nozzle of a spray dryer whereby the solvent from the resulting droplets is evaporated, usually at elevated temperatures, e.g. by the introduction of hot air.

The amount of water-soluble polymer in the spray dried product may be in the range from about 50% to about 99%, in particular about 70% to about 98%, or about 80% to about 95% or about 85% to about 95%, by weight relative to the total weight of the spray dried product comprising TMC278, water-soluble polymer, and optional excipients. The amount of water-soluble polymer in the feed mixture can be calculated based on these percentages and on the amount of solvent used.

The weight:weight ratio of water-soluble polymer to TMC278 is in the range of about 50:1 to about 1:1, or about 20:1 to about 1:1, or about 10:1 to about 1:1, or about 10:1 to about 5:1, for example said weight:weight ratio is about 9:1.

The solvent used in the method of the present invention may be any solvent that is inert towards TMC278 and that is able to dissolve TMC278 and the water-soluble polymer. Suitable solvents include acetone, tetrahydrofuran (THF), dichloromethane, ethanol (anhydrous or aqueous), methanol, and combinations thereof. Of interest are mixtures of methanol and methylene chloride, in particular mixtures of the latter two solvents wherein the v/v ratio methanol/methylene chloride is in the range of about 50:50 to about 90:10; or in the range of about 50:50 to about 80:20, e.g. in a 50:50 ratio, or in a 90:10 ratio.

In one embodiment, the solvent is a mixture of dichloromethane and methanol, the latter in particular being anhydrous methanol. In another embodiment, the solvent is dichloromethane.

The amount of solvent present in the feed mixture will be such that TMC278 and the water-soluble polymer are dissolved and that the feed mixture has sufficient low viscosity for it to be sprayed. In one embodiment the amount of solid materials in the feed mixture is less than 20%, in particular less than 10%, more in particular less than 5%, the percentages expressing the weighed amount of solid materials to the total volume of the feed mixture.

The solvent is removed from the droplets of the feed mixture by the spray-drying step. Preferably the solvent is volatile, with a boiling point of 150° C. or less, preferably 100° C. or less.

The drying gas may be any gas. Preferably, the gas is air or an inert gas such as nitrogen, nitrogen-enriched air or argon. The temperature of the drying gas at the gas inlet of the spray-drying chamber can be from about 25° C. to about 300° C., or from about 60° C. to about 300° C., or from about 60° C. to about 150° C.

The spray-drying is conducted in a conventional spray-drying apparatus comprising a spray-drying chamber, atomizing means for introducing the feed mixture into the spray-drying chamber in the form of droplets, a source of heated drying gas that flows into the spray-drying chamber through an inlet, and an outlet for the heated drying gas. The spray-drying apparatus also comprises a means for collecting the solid pharmaceutical powder that is produced. The atomizing means can be a rotary atomizer, a pneumatic nozzle or, preferably, a high-pressure nozzle.

Suitable rotary atomizers include those having an air turbine drive operating from a high pressure compressed air source, for example a 6 bar compressed air source, which supplies power to an atomization wheel for atomizing the feed mixture. The atomization wheel may be vaned. Preferably, the rotary atomizer is located in the upper part of the spray-drying chamber, for example in the chamber roof, so that the droplets produced dry and fall to the lower part of the chamber. Typically, rotary atomizers produce droplets that have a size in the range of from about 20 to about 225 μm, in particular from about 40 to about 120 μm, the droplet size depending upon the wheel peripheral velocity.

Suitable pneumatic nozzles (including two-fluid nozzles) comprise those that are located in the upper part of the spray-drying chamber, for example in the chamber roof, and operate in so-called "co-current mode". Atomization takes place using compressed air such that the air-liquid ratio is in the range of about 0.5-1.0:1 to about 5:1, in particular from about 1:1 to about 3:1. The feed mixture and the atomizing gas are passed separately to the nozzle head, where the atomization takes place. The size of the droplets produced by pneumatic nozzles depends on the operating parameters and can be in the range from about 5 to 125 μm, in particular from about 20 to 50 μm.

Two-fluid nozzles that operate in so-called "counter-current mode" may also be used. These nozzles operate in a similar way to two-fluid nozzles in co-current modes except that they are located in a lower part of the drying chamber and spray droplets upwards. Typically, counter-current two-fluid nozzles generate droplets, which, when dried, produce particles having a size in the ranging from about 15 to about 80 μm.

A preferred atomizer type for use in the invention is the high-pressure nozzle where liquid feed is pumped to the nozzle under pressure. Pressure energy is converted to kinetic energy, and feed issues from the nozzle orifice as a high-speed film that readily disintegrates into a spray as the film is unstable. The feed is made to rotate within the nozzle using a swirl insert or swirl chamber resulting in cone-shaped spray patterns emerging from the nozzle orifice. Swirl insert, swirl chamber and orifice dimensions together with variation of pressure gives control over feed rate and spray characteristics. The size of the droplets produced by high-pressure nozzles depends on the operating parameters and can be in the range from about 5 to 125 μm, in particular from about 20 to 50 μm.

Suitable atomizing means may be selected depending on the desired droplet size, which depends on a number of factors, such as the viscosity and temperature of the feed mixture, the desired flow rate and the maximum acceptable pressure to pump the feed mixture, have on droplet size. After selecting the atomizing means so that the desired average droplet size is obtained for a feed mixture having a particular viscosity, the mixture is admitted to the spray-drying chamber at a particular flow rate.

The solid dispersion produced by the spray drying process, or produced by the other processes described above {such as solution evaporation and melt extrusion), followed by milling and optional sieving, typically comprises particles having an average effective particle size in the range of from about 10 μm to about 150 μm, or about 15 μm to about 100 μm, particularly about 20 μm to about 80 μm, or 30 μm to about 50 μm, preferably about 40 μm. As used herein, the tenra average effective particle size has its conventional meaning as known to the person skilled in the art and can be measured by art-known particle size measuring techniques such as, for example, sedimentation field flow fractionation, photon correlation spectroscopy, laser diffraction or disk centrifugation. The average effective particle sizes mentioned herein may be related to weight distributions of the particles. In that instance, by "an average effective particle size of about 150 μm" it is meant that at least 50% of the weight of the particles consists of particles having a particle size of less than the effective average of 50 μm, and the same applies to the other effective particle sizes mentioned. In a similar manner, the average effective particle sizes may be related to volume distributions of the particles but usually this will result in the same or about the same value for the average effective particle size.

Optionally, further excipients may be included in the feed mixture, for example to improve properties of the feed mixture or the resulting solid pharmaceutical composition, such as handling or processing properties. Regardless of whether or not excipients are added to the feed mixture, which obviously results in them being incorporated in the solid dispersion, excipients may also be mixed with the resulting solid pharmaceutical composition during formulation into the desired dosage form.

Excipients suitable for inclusion in the pharmaceutical dosage forms comprise surfactants, solubilizers, disintegrants, pigments, flavors, fillers, lubricants, preservatives, thickening agents, buffering agents, and pH modifiers. In particular, surfactants may be added to further improve solubility of the active agent and may also function as wetting agents. Typical surfactants include sodium lauryl sulphate, polyethoxylated castor oil, e.g. Cremophor EL™, Cremophor RH 40™, Vitamin E TPGS, and polysorbates, such as Tween 20™ and Tween 80™, polyglycolized glycerides such as Gelucire™ 44/14 and Gelucire™ 50/13 (available from Gattefossé, France).

Typical pH modifiers that can be added include acids, such as citric acid, succinic acid, tartaric acid; bases; or buffers.

Prior to use, water or other aqueous media such as those containing ingredients to make the solutions more palatable e.g. sugars, such as glucose or flavors, is added to the powders for reconstitution of the invention. The quantity of water that is added is in the range of about 0.5 ml water per mg TMC278 to about 5 ml, or of about 0.5 ml water per mg TMC278 to about 2 ml, or of about 0.5 ml water per mg TMC278 to about 1 ml, e.g. about 0.6 ml/mg TMC278. Addition of water to a powder of TMC278, dispersed in a water-soluble polymer as specified above, generates a supersaturated solution from which the TMC278 active ingredient does not precipitate, which is unexpected.

The powders for reconstitution of the invention will find use mainly in paediatric applications, not only because of the ease of administration to infants and children but also because of the convenience of dosing in function of age and body weight. A further target group are adult patients that have difficulty in swallowing solid dosage forms such as tablets or capsules. Another advantage is that other anti-HIV agents can be combined with TMC278. The powders for reconstitution of the invention show good uptake of the active ingredient and result in good plasma levels, comparable to those obtained with a TMC278 tablet formulation.

The administration of TMC278 as in the present invention may suffice to treat HIV infection, although it may be recommendable to co-administer other HIV inhibitors. The latter preferably include HIV inhibitors of other classes, in particular those selected from NRTIs, PIs and fusion inhibitors. In one embodiment, the other HIV inhibitor that is co-administered is a PI inhibitor. HIV inhibitors that may be co-administered by preference are those used in HAART combinations comprising an NNRTI. For example two further NRTIs or an NRTI and a PI may be co-administered.

In certain instances, the treatment of HIV infection may be limited to only the administration of a powder for reconstitution of TMC278 in accordance with the methodology of this invention, i.e. as monotherapy without co-administration of further HIV inhibitors. This option may be recommended, for example, where the viral load is relatively low, for example where the viral load (represented as the number of copies of viral RNA in a specified volume of serum) is below about 200 copies/ml, in particular below about 100 copies/ml, more in particular below 50 copies/ml, specifically below the detection limit of the virus. In one embodiment, this type of monotherapy is applied after initial treatment with a combination of HIV drugs, in particular with any of the HAART combinations during a certain period of time until the viral load in blood plasma reaches the afore mentioned low viral level.

The powder for reconstitution of TMC278 is preferably administered once daily.

As used herein the term "treatment of HIV infection" relates to a situation of the treatment of a subject being infected with HIV. The term "subject" in particular relates to a human being.

The dose of TMC278 administered, which is determined by the amount of TMC278 in the formulation for use in the invention and the quantity of formulation administered, is selected such that the blood plasma concentration of TMC278 is kept above a minimum blood plasma level. The term "minimum blood plasma level" in this context refers to the lowest efficacious blood plasma level, the latter being that blood plasma level that effectively inhibits HIV so that viral load is below the above-mentioned values. The plasma levels of TMC278 should be kept above said minimum blood plasma level to avoid because at lower levels the virus no longer is suppressed thereby increasing the risk of mutations. Blood plasma levels higher than what is strictly required as minimum level may be preferred to build in a safety margin. The maximum blood plasma levels, i.e. those levels where side effects are experienced are relatively high, i.e. about 500 ng/ml or even higher, such as 1000 ng/ml.

In particular, the blood plasma level of TMC278 is kept at a level between said minimum and maximum blood plasma levels, e.g. in the range of about 20 ng/ml to 1000 ng/ml, or in the range of about 50 ng/ml to about 500 ng/ml, or in the range of about 100 ng/ml to about 500 ng/ml, or in the range of about 200 ng/ml to about 500 ng/ml, or in the range of about 5 ng/ml to about 200 ng/ml, or in the range of 75 ng/ml to about 150 ng/ml, or in the range of about 90 ng/ml to about 100 mg/ml. A suitable daily dose of TMC278 may be in the range of about 0.1 mg to about 3 mg or in the range of about 0.2 mg to about 2.0 mg, or in the range of about 0.2 mg to about 1.0 mg, e.g., about 0.36 mg; each of the foregoing values expressed in mg being mg per kg body weight. The treating physician will be able to determine the dose to be administered by multiplying the mentioned dosages by the body weight of the patient.

The powders for reconstitution of TMC278 in accordance with the present invention provide effective treatment of HIV infection in that the viral load is reduced while keeping viral replication suppressed. The ease of administration may add to the patients' compliance with the therapy.

As used herein, the term "about" has its conventional meaning. When used in relation to a numerical value, it may additionally interpreted to cover values that vary within ±20%, or within ±10%, or within ±5%, or within ±2%, or within ±1% of the numerical value.

EXAMPLES

Example 1

4 g TMC278 base and 36 g PVP-VA 64 are dissolved in 800 ml of a mixture of methanol/methylene chloride 50:50 (v/v). This mixture is spray dried at 80° C. (inlet temperature) using a Mini Spray Dryer B-191 (Büchi, Switzerland). The flow control was set at 800 N 1/h pressurized air, the aspirator at 100% and the pump at 50%. Afterwards, the resulting powders were post dried in a vacuum dryer (Christ Alpha, Medizinischer Apparatebau, OsterodelHarz, Germany) for 44 hours.

Example 2

4 g TMC278 base, 34 g PVP-VA 64 and 2 g Cremophor EL are dissolved in 800 ml of a mixture of methanol/methylene chloride 50:50 (v/v). This mixture is the spray dried at 80° C. (inlet temperature) using a Mini Spray Dryer B-191 (Büchi, Switzerland). The flow control was set at 800 N 1/h pressurized air, the aspirator at 100% and the pump at 50%. Afterwards, the resulting powders were post dried in a vacuum dryer (Christ Alpha, as above) for 44 hours.

Dissolution:

The powders for reconstitution of example 1 and 2 were tested on dissolution. During the dissolution test, the powders for reconstitution of TMC278 was suspended into 50 ml of water and the resulting suspension was added into 500 ml of the 0.01 M HCl aqueous solution serving as dissolution medium resulting in a final suspension volume of 550 ml. At each time point, 5.0 ml of the final suspension was removed and the volume was compensated by adding 5.0 ml of fresh dissolution medium. So, to calculate the % of the substance at each time period, the amount which was removed until that time period was subtracted from labelled amount and the remaining amount was considered as 100% concentration for that time period. TMC278 reached a steady state plateau at 5 min in both cases.

Animal Study:

Six male beagle dogs, approximately 1 to 3 years old and weighing between 8 and 14 kg at the start of the experimental phase, were used in the present study. The dogs were given free and continuous access to water. Each dosing day, the dogs were deprived of food for approximately 18 hours before dosing, and were fed immediately after dosing with free access to food until during a period of 6 hours starting after dosing. Oral dosing in the first phase of the study was done by gavaging 40 ml of the freshly prepared aqueous suspensions of TMC278. The two suspensions were administered to 3 dogs each. After a washout period of 14 days, all 6 dogs were dosed by administration of a tablet of TMC278.HCl, providing a dose of 50 mg eq. per animal. The dosing scheme is presented in Table 1.

Per dog, two vials each containing 25 mg of TMC278, formulated as TMC278/PVP-VA 64 10/90% (weight/weight or w/w) powder for reconstitution (dogs 1, 2, 3), or two vials each containing 25 mg of TMC278, formulated as TMC278/PVP-VA 64/Cremophor EL 10/85/5% (m/m/m) powder for reconstitution (dogs 4, 5, 6) were used. For each dog, a tablet for clinical use containing 50 mg eq. of TMC278 hydrochloride(HCl salt of TMC278) was supplied.

Blood samples (1 ml on EDTA) were taken from a jugular vein from the dogs at 0 (=predose), 0.5 (30 min), 1, 2, 4, 8, 24, 32 and 48 h after dose administration. After sampling, blood samples were protected from light immediately. The samples were centrifuged within two hours of blood sampling at about 1900×g for approximately 10 minutes at room temperature to allow plasma separation. Immediately thereafter, plasma was separated, transferred into a second tube and stored in the freezer within two hours after the start of centrifugation. At all times, blood and plasma samples were protected from light. Plasma samples were stored in a freezer <−18° C. until analysis. The plasma samples were analysed using LC-MS/MS.

Individual plasma concentration versus time profiles were subjected to a non-compartmental pharmacokinetic analysis using validated WinNonlin software v4.0.1a. Peak concentrations ($C_{max}$), corresponding peak times ($T_{max}$), half-lives ($t_{1/2}$) and AUC values were determined for TMC278. Mean (n=3 or 6, wherein n is the number of dogs, ±SD) or median plasma concentrations of TMC278 were calculated per formulation and per sampling time. Mean (n=3 or 6, ±SD) pharmacokinetic parameters per formulation were also calculated. In addition the relative bioavailability ($F_{rel}$) of TMC278 dosed with the powders for reconstitution versus the clinical tablet was estimated individually.

Figure 1:
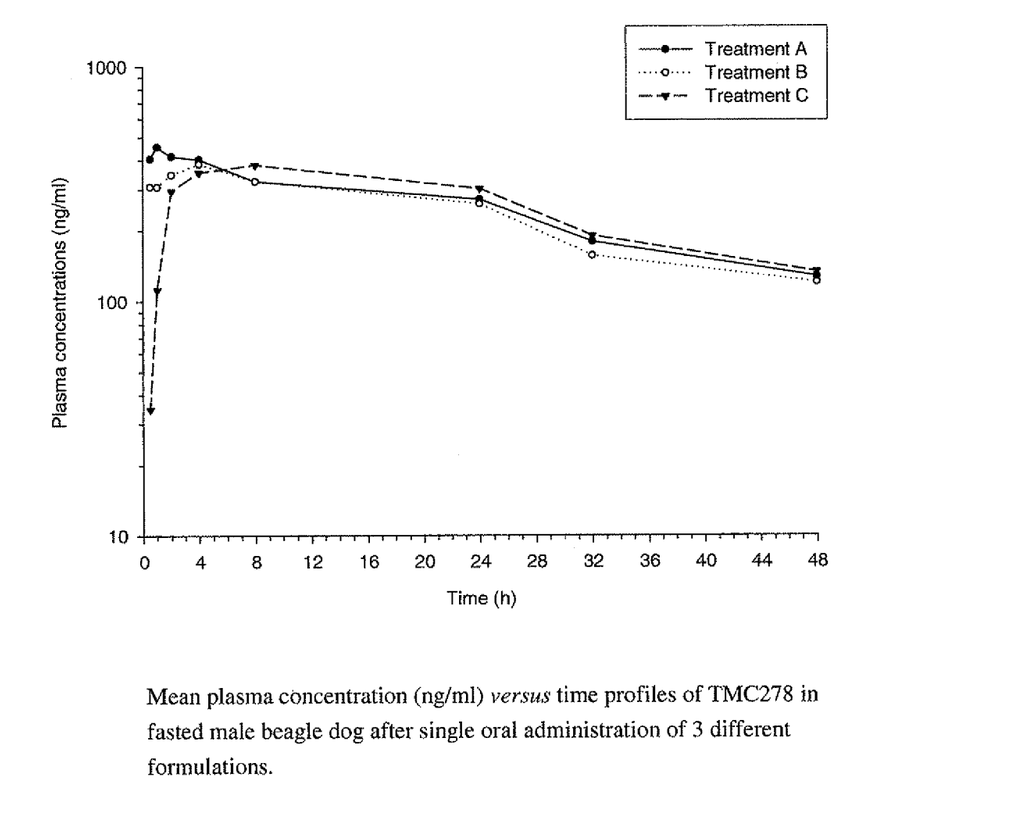

Individual and mean (n=3 or 6, ±SD) or median plasma concentrations in fasted male beagle dogs and some basic pharmacokinetic parameters of TMC278 after single oral dosing of a suspension of the powders for reconstitution or a tablet of TMC278, are reported in Table 2 to Table 4. The individual bioavailabilities are represented in Table 5. Mean plasma concentration versus time profiles of TMC278 are depicted in FIG. 1.

After oral administration of a suspension of a TMC278/PVP-VA 64 10/90% (w/w) powder for reconstitution (treatment A) at 50 mg of TMC278 (actual dose range: 4.31-5.75 mg/kg), high plasma concentrations were already observed at ½ h after dosing, with maximum levels ($C_{max}$) at ½ h to 4 h post-dosing amounting on average to 544 ng/ml. Afterwards, plasma levels declined very slowly, with a mean half-life between 32 and 48 h ($t_{1/2, 32-48 h}$) of 34.5 h. As the half-lives were long, the $AUC_{0-inf}$ values could not be calculated adequately. Therefore the exposure to TMC278 was expressed by $AUC_{0-48 h}$ values, which averaged to 11900 ng.h/ml.

After oral dosing of a suspension of a TMC278/PVP-VA 64/Cremophor EL™ 10/85/5% (m/m/m) powder for reconstitution (treatment B) at 50 mg of TMC278 (actual dose range: 3.83-6.06 mg/kg), plasma levels were already high at 0.5 h post-dose and peak plasma concentrations ($C_{max}$) were reached within 0.5 h to 8 h post-dose. $C_{max}$ values amounted on average to 443 ng/ml, after which plasma levels declined very slowly, with a half-life between 32 and 48 h ($t_{1/2, 32-48 h}$) of 46.8 h on average. As the half-lives were long, the $AUC_{0-inf}$ values could not be calculated adequately. Therefore the exposure to TMC278 was expressed by $AUC_{0-48 h}$ values. The mean exposure amounted to 11200 ng.h/ml.

After oral administration of the clinical tablet of TMC278.HCl (treatment C) at 50 mg eq. of TMC278 (actual dose range: 3.88-6.25 mg/kg), absorption was slower than with the suspensions. Peak plasma levels ($C_{max}$) were reached between 2 h and 24 h post-dose and amounted on average to 501 ng/ml. Afterwards, the decline in plasma concentrations was very slow, with a mean half-life between 32 and 48 h ($t_{1/2, 32-48}$) of 45.7 h. As the half-lives were long, the $AUC_{0-inf}$ values could not be calculated adequately. Therefore exposure to TMC278 was expressed by $AUC_{0-48 h}$ values, which amounted to 12300 ng.h/ml on average.

The relative bioavailability based on the individual $AUC_{0-48 h}$ values) of the formulation containing TMC278/PVP-VA 64 10/90% vs. the clinical tablet, ranged between 69 and 89%. The relative bioavailability ($F_{rel}$, based on the individual $AUC_{0-48 h}$ values) of the formulation containing TMC278/PVP-VA 64/Cremophor EL 10/85/5% vs. the clinical tablet, was estimated at 85 to 157%.

Tables

TABLE 1

Day of dosing, dose, formulation, group and feeding condition of the male beagle dogs used in the present study.

| Day of Dosing | Total dose (mg (eq.)) | Treatment | Group | Condition |
|---|---|---|---|---|
| Day 0 | 50 | A[1] | 1 | fasted, fed immediately after dosing |
| (Jul. 24, 2006) | 50 | B[2] | 2 | fasted, fed immediately after dosing |
| Day 14 | 50 | C[3] | 1 | fasted, fed immediately after dosing |
| (Aug. 07, 2006) | 50 | C[3] | 2 | fasted, fed immediately after dosing |

[1]Treatment A: 2x TMC278/PVP-VA 64 10/90% (m/m) powder.
[2]Treatment B: 2x TMC278/PVP-VA 64/Cremophor EL 10/85/5% (m/m/m) powder.
[3]Treatment C: one tablet of 50 mg eq. of TMC278.

TABLE 2

Individual and mean (n = 3, ±SD) plasma concentrations and some basic pharmacokinetic parameters of TMC278 after single oral administration at 50 mg of TMC278 of a formulation containing TMC278/PVP-VA 64 10/90% in fasted male beagle dogs.

| | Treatment | | | | |
|---|---|---|---|---|---|
| | A (TMC278/PVP-VA 64 10/90% (m/m) powder) | | | | |
| | Day | | | | |
| | 0 | | | | |
| | Actual dose (mg eq./kg) | | | | |
| | 4.83 | 4.31 | 5.75 | | |
| | Subject | | | | |
| Time (h) | 1 | 2 | 3 | Mean | SD |
| 0 | <1.00 | <1.00 | <1.00 | <1.00 | — |
| 0.5 | 297 | 140 | 778 | 405 | 332 |
| 1 | 428 | 323 | 615 | 455 | 148 |
| 2 | 407 | 373 | 464 | 415 | 46 |
| 4 | 370 | 427 | 409 | 402 | 29 |
| 8 | 299 | 371 | 301 | 324 | 41 |
| 24 | 212 | 259 | 342 | 271 | 66 |
| 32 | 128 | 186 | 222 | 179 | 47 |
| 48 | 92.2 | 145 | 143 | 127 | 30 |
| $C_{max}$ (ng/ml) | 428 | 427 | 778 | 544 | 202 |
| $T_{max}$ (h) | 1 | 4 | 0.5 | 2 | 2 |
| $t_{1/2,\ 32-48\ h}$ (h) | 33.8 | 44.5 | 25.2 | 34.5 | 9.7 |
| $AUC_{0-48\ h}$ (ng·h/ml) | 9910 | 12300 | 13600 | 11900 | 1870 |
| $AUC_{0-inf}$ (ng·h/ml) | 14400 [1] | 21600 [1] | 18800 [1] | 18300 [1] | 3620 |
| $AUC_{Extrapolated}$ (%) | 31.2 | 43.1 | 27.7 | 34.0 | 8.1 |

[1] calculated with >25% extrapolation

TABLE 3

Individual and mean (n = 3, ±SD) plasma concentrations and some basic pharmacokinetic parameters of TMC278 after single oral administration at 50 mg of TMC278 of a formulation containing TMC278/PVP-VA 64/Cremophor EL 10/85/5% in fasted male beagle dogs.

| | Treatment | | | | |
|---|---|---|---|---|---|
| | B (TMC278/PVP-VA 64/Cremophor EL 10/85/5% (m/m/m) powder) | | | | |
| | Day | | | | |
| | 0 | | | | |
| | Actual dose (mg eq./kg) | | | | |
| | 3.83 | 6.06 | 5.26 | | |
| | Subject | | | | |
| Time (h) | 4 | 5 | 6 | Mean | SD |
| 0 | <1.00 | <1.00 | <1.00 | <1.00 | — |
| 0.5 | 284 | 174 | 466 | 308 | 147 |
| 1 | 289 | 205 | 427 | 307 | 112 |
| 2 | 379 | 260 | 400 | 346 | 76 |
| 4 | 485 | 317 | 352 | 385 | 89 |
| 8 | 339 | 379 | 253 | 324 | 64 |
| 24 | 292 | 310 | 176 | 259 | 73 |
| 32 | 177 | 193 | 99.4 | 156 | 50 |
| 48 | 153 | 136 | 70.7 | 120 | 43 |
| $C_{max}$ (ng/ml) | 485 | 379 | 466 | 443 | 57 |
| $T_{max}$ (h) | 4 | 8 | 0.5 | 4 | 4 |
| $t_{1/2,\ 32-48\ h}$ (h) | 76.1 | 31.7 | 32.6 | 46.8 | 25.4 |
| $AUC_{0-48\ h}$ (ng·h/ml) | 12600 | 12400 | 8520 | 11200 | 2290 |
| $AUC_{0-inf}$ (ng·h/ml) | 29400 [1] | 18600 [1] | 11800 [1] | 19900 [1] | 8830 |
| $AUC_{Extrapolated}$ (%) | 57.2 | 33.4 | 28.0 | 39.5 | 15.5 |

[1] calculated with >25% extrapolation

TABLE 4

Individual and mean (n = 6, ±SD) or median plasma concentrations and some basic pharmacokinetic parameters of TMC278 after single oral administration of a clinical tablet of TMC278•HCl at 50 mg eq. in fasted male beagle dogs.

| | Treatment | | | | | | | |
|---|---|---|---|---|---|---|---|---|
| | C (tablet of 50 mg eq. of TMC278) | | | | | | | |
| | Day | | | | | | | |
| | 14 | | | | | | | |
| | Actual dose (mg eq./kg) | | | | | | | |
| | 4.90 | 4.55 | 5.95 | 3.88 | 6.25 | 5.15 | | |
| | Subject | | | | | | | |
| Time (h) | 1 | 2 | 3 | 4 | 5 | 6 | Mean | SD |
| 0 | <1.00 | <1.00 | <1.00 | 2.43 | <1.00 | <1.00 | <1.00 [1] | — |
| 0.5 | <1.00 | 7.63 | 69.1 | 150 | 13.5 | 55.7 | 34.6 [1] | — |
| 1 | <1.00 | 124 | 86.3 | 348 | 99.0 | 160 | 112 [1] | — |
| 2 | 1.27 | 367 | 252 | 536 | 263 | 351 | 295 | 176 |
| 4 | 19.1 | 647 | 346 | 369 | 518 | 225 | 354 | 220 |
| 8 | 237 | 558 | 581 | 249 | 500 | 161 | 381 | 185 |
| 24 | 370 | 407 | 362 | 203 | 344 | 121 | 301 | 113 |
| 32 | 251 | 275 | 213 | 125 | 212 | 63.3 | 190 | 80 |
| 48 | 158 | 204 | 147 | 115 | 130 | 42.4 | 133 | 54 |
| $C_{max}$ (ng/ml) | 370 | 647 | 581 | 536 | 518 | 351 | 501 | 117 |
| $T_{max}$ (h) | 24 | 4 | 8 | 2 | 4 | 2 | 7 | 9 |
| $t_{1/2,\,32\text{-}48\,h}$ (h) | 24.0 | 37.1 | 29.9 | 133.0 | 22.7 | 27.7 | 45.7 | 43.1 |
| $AUC_{0\text{-}48\,h}$ (ng·h/ml) | 11100 | 17900 | 15200 | 9530 | 14600 | 5440 | 12300 | 4480 |
| $AUC_{0\text{-}inf}$ (ng·h/ml) | 16500 [2] | 28800 [2] | 21500 [2] | 31600 [2] | 18800 | 7140 | 20700 | 8830 |
| $AUC_{Extrapolated}$ (%) | 33.1 | 38.0 | 29.5 | 69.8 | 22.6 | 23.7 | 36.1 | 17.5 |

[1] median value
[2] calculated with >25% extrapolation

TABLE 5

Individual relative bioavailability of TMC278 in fasted male beagle dogs after single oral administration at 50 mg eq.

| | $AUC_{0\text{-}48\,h}$ (ng·h/ml) | | | | | |
|---|---|---|---|---|---|---|
| | Subject | | | | | |
| Treatment | 1 | 2 | 3 | 4 | 5 | 6 |
| C (tablet of 50 mg eq. of TMC278) | 11100 | 17900 | 15200 | 9530 | 14600 | 5440 |
| A (TMC278/PVP-VA 64 10/90% (m/m) powder) | 9910 | 12300 | 13600 | — | — | — |
| B (TMC278/PVP-VA 64/Cremophor EL 10/85/5% (m/m/m) powder) | — | — | — | 12600 | 12400 | 8520 |
| $F_{rel}$ (%) | 89% | 69% | 89% | 132% | 85% | 157% |

The invention claimed is:

1. A method of treating an infant, child or elderly patient infected with HIV, said method comprising the oral administration once daily to said infant, child or elderly patient of a supersaturated solution consisting of 4-[[4-[[4-(2-cyanoethenyl)-2,6-dimethyl-phenyl]amino]-2-pyrimidinyl]-amino]benzonitrile or a stereoisomeric form thereof, and a water-soluble copolymer of vinylpyrrolidone and vinyl acetate in an aqueous medium wherein in the supersaturated solution the weight: weight ratio of copolymer of vinylpyrrolidone and vinyl acetate to 4-[[4-[[4-(2-cyanoethenyl)-2,6-dimethyl-phenyl]amino]-2-pyrimidinyl]-amino]benzonitrile or a stereoisomeric form thereof is about 9:1.

2. The method according to claim 1 wherein the supersaturated solution consists of (E)- 4[[4-[[4-(2-cyanoethenyl)-2,6-dimethyl-phenyl]amino]-2-pyrimidinyl]-amino]benzonitrile.

* * * * *